(12) United States Patent
McKiernan et al.

(10) Patent No.: US 8,680,362 B2
(45) Date of Patent: Mar. 25, 2014

(54) SUBSTRATE COATED WITH A HYDROPHILIC ELASTOMER

(75) Inventors: Robin Lynn McKiernan, Mason, OH (US); Steve Daryl Smith, Fairfield, OH (US); Kemal Vatansever Catalan, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 174 days.

(21) Appl. No.: 13/169,113

(22) Filed: Jun. 27, 2011

(65) Prior Publication Data
US 2011/0319848 A1 Dec. 29, 2011

Related U.S. Application Data

(60) Provisional application No. 61/359,121, filed on Jun. 28, 2010.

(51) Int. Cl.
*A61F 13/15* (2006.01)
*B32B 27/00* (2006.01)

(52) U.S. Cl.
USPC ........................................ 604/372

(58) Field of Classification Search
USPC ................. 604/372, 373, 365, 366, 367; 428/473.5; 442/118
See application file for complete search history.

(56) References Cited

U.S. PATENT DOCUMENTS

| 3,567,798 | A | 3/1971 | Haefele et al. |
| 2002/0010267 | A1* | 1/2002 | Klaerner et al. ................. 525/91 |
| 2004/0158212 | A1* | 8/2004 | Ponomarenko et al. ...... 604/367 |
| 2008/0200331 | A1 | 8/2008 | Daniel et al. |
| 2010/0228213 | A1 | 9/2010 | Berland et al. |

FOREIGN PATENT DOCUMENTS

| EP | 0566896 | 10/1993 |
| EP | 0887368 | 12/1998 |
| WO | WO 2005/014065 A1 | 2/2005 |

OTHER PUBLICATIONS

International Search Report, PCT/US2011/042116, mailed Oct. 7, 2011, 10 pages.
International Search Report, PCT/US2011/042117, dated Sep. 6, 2011, 10 pages.

* cited by examiner

*Primary Examiner* — Jacqueline F. Stephens
(74) *Attorney, Agent, or Firm* — Andrew A Paul

(57) ABSTRACT

Substrates, coated with a block copolymer comprising at least four blocks being at least two hard blocks, one soft block and one hydrophilic block, wherein a the soft block is sandwiched between the hard blocks.

18 Claims, No Drawings

SUBSTRATE COATED WITH A HYDROPHILIC ELASTOMER

CROSS REFERENCE TO RELATED APPLICATION

This application claims the benefit of U.S. Provisional Application No. 61/359,121 filed on Jun. 28, 2010.

FIELD OF THE INVENTION

The present disclosure relates to substrates, such as woven substrates, nonwoven substrates, films, and laminates, comprising a hydrophilic elastomeric water vapor permeable coating. The coating is intended to increase hydrophilicity of the substrates and for example accommodate bending and/or stretching of the substrate without breakage of the coating.

The disclosure also relates to the application of such substrates in absorbent articles, such as diapers, adult incontinence articles, wipes and feminine hygiene products, such as catamenial devices, sanitary napkins.

Further a process of making substrates comprising the hydrophilic elastomeric water vapor permeable coating is described.

BACKGROUND OF THE INVENTION

Absorbent articles such as baby diapers, feminine hygiene products, adult incontinence products or wipes are known in the art and substrates made of synthetic polymer material, synthetic fibers and/or natural fibers are commonly used in such absorbent articles, for example, as topsheet material, as core wrap to enclose the absorbent material in the absorbent core, but also in acquisition systems of absorbent cores.

Often, such substrates are per se hydrophobic. However, for many applications in absorbent articles it is necessary to have substrates of a suitable hydrophilicity.

A topsheet, for example, is typically a substrate designed to provide an interface between the wearer and the absorbent core of an absorbent articles as well as to provide the first point of contact for any bodily waste exuded by the wearer. Topsheets may be made form a film, such as an apertured film, or they may be made of nonwoven webs. These films or the nonwoven webs often need to be rendered hydrophilic.

A common method for rendering substrates hydrophilic is coating the surface of the substrate with hydrophilic surfactants. However, surfactants may be washed off during use when the absorbent article is wetted.

This may typically lead to a decrease in hydrophilicity of the substrate and for example in a decrease in the substrates permeability leading to a performance reduction during use on absorbent articles comprising such substrates.

While durable hydrophilic polymer coatings, when used instead of the surfactants, may be more resistant to washing off, they can also be brittle which can lead to breaking of the coating when the substrate is stretched or bended, for example due to process steps or typical movements of the wearer.

Thus, there is a continuing need for further improving the properties of hydrophilic coatings, such as for example improving their mechanic stability towards bending and/or stretching of the substrates.

The inventors have developed new substrates coated with a specific block copolymer as described herein. The resulting coated substrates have been found to show a good hydrophilicity as well as a good stability of the coating upon bending and/or stretching of the substrates.

SUMMARY OF THE INVENTION

A substrate coated with a block copolymer is described. The block copolymer is obtainable by preparing a sequence of soft block(s) (A) and hard blocks (B), the sequence comprising at least three blocks being at least a first soft block, a first hard block and a second hard block wherein the first soft block is sandwiched between the first and second hard blocks (B), combining the sequence of soft block(s) and hard blocks with a hydrophilic block (C) block, or combining the sequence of soft block(s) and hard blocks with a hydrophilic block precursor and subsequently transforming the hydrophilic block precursor into the hydrophilic block (C).

Without wishing to be bound by theory, it is believed that due to the specific selection of the four or more blocks of the block copolymer a coating providing good hydrophilicity, paired with good stability of the coating which can help to accommodate bending and/or stretching of the substrate.

It is for example believed that the good hydrophilicity is influenced by the low contact angle of the block copolymer and potentially also with the high water vapor transmission rate of the block copolymers, and that the good stability of the coating results from its elastic extensibility.

DETAILED DESCRIPTION OF THE INVENTION

Definition of Terms

"Block copolymer" refers to copolymers comprising different polymeric subunits (blocks) wherein the individual blocks are covalently bound to each other.

The individual "blocks" are typically composed of monomeric units. The term "monomeric unit", instead of monomer, is used in order to refer to a sequence of polymerized monomers having the same chemical composition irrespective of their synthesis. For example, polystyrene is a polymer obtained by the polymerization of the monomer styrene. Polystyrenesulfonate on the other hand may be obtained by polymerization of styrenesulfonate monomers or by sulfonation of polystyrene. Irrespective of the chosen synthesis, it comprises monomeric units of styrene sulfonate. Herein the "block length" (i.e. the length of an individual block) is expressed by the number of same or similar monomeric units which are directly covalently bound to each other. Generally, a block comprises at least 10 monomeric units.

The "hydrophilic block" herein refers to a block which is added to the sequence of soft block(s) and hard blocks in order to enhance the affinity of the resulting block copolymer towards water. Typically, the hydrophilic block is comprised of, or consists of, hydrophilic monomeric units. Generally, monomeric units that enhance the affinity of the resultant polymer towards water will be considered hydrophilic. Typical hydrophilic monomeric units comprise functional groups such as polar and/or charged functional groups, for example hydrophilic monomeric units comprise one or more functional groups selected from the group consisting of acid groups in their free acid and salt form, ether groups, amine functionalized groups, quaternary ammonium groups, alcoholic groups and combinations thereof. Typically, the hydrophilic block increases the hydrophilicity of the block copolymer. For example, the block copolymer may have a smaller contact angle than the sequence of soft block(s) and hard blocks.

"Soft block" as used herein refers to a polymeric block having a glass transition temperature of below 20° C., or below 10° C., for example below 0° C.

"Hard block" as used herein refers to a polymeric block having a glass transition temperature of at least 40° C., or at least 80, for example at least 100° C.

"Elastomeric" when used herein means that the material will exhibit stress induced deformation that is partially or completely reversed upon removal of the stress.

"Absorbent article" herein refers to an article generally capable of absorbing and storing exudates discharged from the body. Absorbent articles are typically placed against or in proximity to the body of a wearer to absorb and contain the exudates discharged from the body, such as urine, blood or menses.

Typical absorbent articles may be diapers, such as pant-like diapers or taped diapers, feminine hygiene products, such as sanitary napkins tampons or panty liners; adult incontinence briefs, adult incontinence undergarments, absorbent inserts, wipes and the like.

"Diaper" refers to an absorbent article that is intended to be worn by wearer about the lower torso to absorb and contain exudates discharged from the body.

Diapers are typically worn by infants (e.g. babies or toddlers) and may be taped diapers which are provided with unfastened fastening elements or as in pant-like diapers having fixed sides in order to from a waist and leg openings. The fixed sides may be permanently or refastenably fixed to each other. Generally, pant-like diapers are placed in position on the wearer by inserting the wearer's legs into the leg openings and sliding the pant-like diaper into position about the wearer's lower torso.

"Disposable" refers to items that are intended to be discarded after a limited number of uses, frequently a single use (i.e., the original absorbent article as a whole is not intended to be laundered or reused as an absorbent article, although certain materials or portions of the absorbent article may be recycled, reused, or composted). For example, certain disposable absorbent articles may be temporarily restored to substantially full functionality through the use of removable/replaceable components but the article is nevertheless considered to be disposable because the entire article is intended to be discarded after a limited number of uses. Typically, the absorbent articles referred to herein are disposable, for example disposable diapers.

"Absorbent core" refers to a member of an absorbent article that is intended to absorb and store exudates discharged from the body. The absorbent core typically comprises absorbent material and, optionally, a core wrap. Optionally, the absorbent core may comprise a glue, such as a micro-fiber glue.

"Absorbent material" refers to liquid absorbent materials such as for example soft materials providing a rather fluffy structure with a lot of empty space, such as comminuted wood pulp, creped cellulose wadding, chemically stiffened, modified or cross-linked cellulosic fibers all of which are herein generally referred to as "airfelt". Absorbent material also refers to superabsorbent polymer material, such as super absorbent polymer particles, fibers or foams and mixtures of superabsorbent polymer material with airfelt.

In certain embodiments, absorbent materials may refer to paper towels, tissue, nonwovens, absorbent foams/sponges, cloth and the like. The absorbent material may advantageously be compressible, conformable, non-irritating to the wearer's skin, and capable of absorbing and retaining liquids such as urine and certain other body exudates.

"Substrate" herein refers to woven webs, nonwoven webs, polymeric films, metal foils, as well as laminates of two or more layers selected from the group consisting of polymeric films, nonwoven webs, woven webs, polymeric films metal foils and combinations thereof.

"Nonwoven web" as used herein refers to a manufactured web of directionally or randomly orientated fibers, bonded by friction, and/or cohesion and/or adhesion, excluding paper and products which are woven, knitted, tufted, stitch-bonded incorporating binding yarns or filaments, or felted by wet-milling, whether or not additionally needled. The basis weight of nonwoven fabrics is usually expressed in grams per square meter ($g/m^2$) and can be determined according to EDANA method 40.3-90.

"Woven webs" typically include materials made form yarns or fibers which are which are woven, knitted, tufted, stitch-bonded. In some embodiments, they may be felted by wet-milling.

"Films" typically include substrates which are not made of fibers or yarns. For example, films may be made from polymeric material by extrusion processes. Films may be apertured films or continuous (i.e. not apertured) films.

Substrates

Suitable substrates include woven webs, nonwoven webs or films, such as polymeric web materials, (apertured formed) thermoplastic films, (apertured) plastic films, hydroformed thermoplastic films, reticulated thermoplastic films and combinations, e.g. laminates thereof.

In some embodiments, the substrates may be porous foams, reticulated foams, and thermoplastic scrims; paper tissue or combinations thereof.

Suitable substrates include web material (e.g., woven or nonwoven web) comprising natural fibers or synthetic fibers or combinations thereof.

Examples of natural fibers may include cellulosic natural fibers, such as fibers from hardwood sources, softwood sources, or other non-wood plants, animal fibers such as wool, silk, fur, and hair.

The synthetic fibers can be any material, such as, but not limited to, those selected from the group consisting of polyesters (e.g., polyethylene terephthalate), polyolefins, polypropylenes, polyethylenes, polyethers, polyamides, polyesteramides, polyvinylalcohols, polyhydroxyalkanoates, polysaccharides, and combinations thereof.

Further, the synthetic fibers can be a single component (i.e., single synthetic material or mixture makes up entire fiber), bi-component (i.e., the fiber is divided into regions, the regions including two or more different synthetic materials or mixtures thereof and may include co-extruded fibers and core and sheath fibers) and combinations thereof. Bi-component fibers can be used as a component fiber of the web material, and/or they may be present to act as a binder for the other fibers present in the web material.

Any or all of the synthetic fibers may be treated before, during, or after manufacture to change any desired properties of the fibers. For example, the fibers may be coated with the block copolymer described herein instead of or in addition to applying the block copolymer to the substrate. The terms "coated substrate" or "substrate coated with" as used herein are intended to encompass such embodiments as well.

In some embodiments the substrates herein may be or may comprise a nonwoven web material, whereby said nonwoven web may be manufactured by a wide number of known techniques. Non-limiting examples of techniques include spun-bonding, carding, wet-laid, air-laid, melt-blown, needle-punching, mechanical entangling, thermo-mechanical entangling, hydroentangling, calender bonding and combination thereof.

The substrate may be or may comprise a laminate web of two or more nonwoven webs. The laminate web may comprise spunbond layer(s) (S), and/or meltblown layer(s) (M), and/or carded layer(s). Suitable laminate webs include, but are not limited to, SS, SSS, SMS, SMMS or SMMMS. In some embodiments, the laminate web may comprise nanofibers having a diameter of less than 1 µm.

The substrates may further comprise laminates of nonwoven layers with film layers.

The substrates herein have a basis weight between about 5 to 100 g/m². Where the substrate is comprised by, or forms, or is used for manufacturing of the topsheet, core wrap and/or a layer of the acquisition system it may have for example a basis weight between about 5 to 100 g/m², or between about 10 to 40 g/m², or between about 10 to 30 g/m². Where the substrate is used as, or in a wipe, it may for example have a basis weight between about 15 to 100 g/m², or between about 30 to 95 g/m², or between about 40 to 85 g/m², or between about 45 to 75 g/m².

In some embodiments, the block copolymer herein may be used to coat a metal foil, such as aluminium foil. Coated metal foil may for example be used to pack one ore more absorbent articles.

For example metal foil may be coated on one side. When sued to pack absorbent articled, the coated side of the metal foil may face towards the packed article. In one embodiment, the packed article may be a wipe, for example a wet wipe. Optionally, the metal foil may be laminated with additional film layers, such as layers of polyethylene or polypropylene.

Block Copolymers

The block-copolymer comprises at least four blocks being at least one soft block (A), sandwiched between at least two hard blocks (B) and at least one hydrophilic block (C).

Generally, block copolymers of such a structure may be obtained by any suitable method known to those skilled in the art. For example block copolymers may be obtained by sequential polymerization of chemically different monomers and/or by bonding preformed polymeric blocks to each other via suitable chemical reactions.

For example, the block copolymers described herein may be obtained by preparing a sequence of soft blocks(s) (A) and hard blocks (B), the sequence comprising at least three blocks being at least a first soft block, a first hard block and a second hard block wherein the first soft block is sandwiched between the first and second hard blocks (B), adding a hydrophilic block (C) to the sequence of soft and hard blocks.

The block copolymers may be prepared by living anionic polymerization.

B-A-B-C block copolymers may for example be obtained by the following steps:

a) living anionic polymerization of first hard block B, wherein first hard block B has a living end;

b) to the living end of first hard block B, soft block A is polymerized to give B-A, wherein A has a living end;

c) to the living end of soft block A, second hard block B is polymerized to give the sequence B-A-B, wherein second hard block has a living end; optionally repeating step b) and/or c) in any order to obtain for example a sequence B-(A-B)$_n$- wherein n is an integer being larger than 1.

d) to the living end of second hard block B, or optionally to the living end of the last block in embodiments wherein steps b) and/or c) have been repeated, the hydrophilic block is added;

and optionally further repeating step b), c) and/or d) in any order

Addition of the hydrophilic block may be accomplished by polymerizing an additional block to the living chain end, which is either hydrophilic or subsequently rendered hydrophilic by suitable chemical reactions.

Generally, the sequence of soft block(s) and hard blocks may have at least two glass transition temperatures $Tg_1$ and $Tg_2$, respectively. Herein, glass transition temperatures $Tg_1$ and $Tg_2$ may for example be measured on a sample of the sequence of soft block(s) and hard blocks before the hydrophilic block is added.

$Tg_1$ will typically be a lower temperature than $Tg_2$. For example, $Tg_1$ is below or equal to 20° C. and/or $Tg_2$ is above or equal to 40° C. $Tg_1$ and $Tg_2$ typically differ by at least 20° C.

After the addition of the hydrophilic block the Tg's of the block copolymer may be measured again. In such instances, an additional $Tg_{Hydrophil}$, which has not been detected for the sequence of soft and hard blocks, may be detected.

In certain embodiments, $Tg_{Hydrophil}$ may vary when water is added to the block copolymer. Typically, $Tg_{Hydrophil}$ decreases when water is added.

In embodiments wherein the sequence of soft and hard blocks has more than two different glass transition temperatures, $Tg_1$ refers to the glass transition temperature of the soft block having the highest Tg among all soft blocks, i.e. among all blocks having a glass transition temperature of less than 20° C., and $Tg_2$ refers to the glass transition temperature of the hard block having the lowest Tg of all hard blocks, i.e. among all blocks having a glass transition temperature of above 40° C.

In some embodiments, the block-copolymer may be a tetra-block-copolymer, i.e. comprises only four blocks of the general sequence (hard block)-(soft block)-(hard block)-(hydrophilic block), i.e. B-A-B-C.

The block copolymer may also be a multi-block-copolymer of the general structure -(B-A-B-C)$_n$-, wherein n is an integer typically having a value between 2 and 10. Such a multi-block copolymers may be obtained by preparing block copolymers of the structure B-A-B-C and linking them to each other by suitable chemical reactions known to the person skilled in the art in order to obtain -(B-A-B-C)$_n$-.

Also, in some embodiments multi-block-copolymers, the sequence of soft blocks and hard blocks may comprise more than one soft and two hard blocks. In such embodiments, the sequence of soft and hard blocks may be alternating, for example -A-B-A-B-A-B-.

Further, in some embodiments the block copolymer may comprise two hydrophilic blocks attached to each end of the sequence of soft block(s) and hard blocks, such as C-B-(A-B)$_n$-C, wherein n is an integer larger than or equal to 1, for example n may be in a range from 1 up to 10, or 2 up to 5.

Typically, the hydrophilic block is not attached to a soft block.

While the different hard blocks may be composed of different monomeric units, it may be advantageous in order to simplify the synthesis that the hard blocks are composed of the same monomeric units. This may also apply to embodiments having more than one soft block. Thus, in certain embodiments, the block-copolymer may be a terpolymer, i.e. it comprises soft, hard and hydrophilic blocks, wherein all soft blocks are composed of the same soft monomeric units, all hard are composed of the same hard monomeric units and all hydrophilic blocks are composed of the same hydrophilic monomeric units.

To provide good transport of water based fluids through the coating into the superabsorbent polymer particles, the block copolymer may typically exhibit a WVTR (Water Vapor Transmission Rate) of at least 600 g/m$^2$/day, or at least 1000 g/m$^2$/day, or at least 3000 g/m$^2$/day, or at least 5000 g/m$^2$/day, or even at least 6000 g/m$^2$/day, when processed into a film and measured according to the WVTR method described herein. In some embodiments, the WVTR may generally be below 20000 g/m$^2$/day.

In order to accommodate swelling of the superabsorbent polymer particles, the block copolymer may exhibit a wet-elongation at break value of at least 300%, or at least 400% for example at least 1000% when processed into a film and measured according to the method herein. In some embodiments, the wet elongation at break may not be greater than 10000%. Also, it may be desirable for its application on superabsorbent particles, that the coating exhibits such extensibility in dry and in wet state.

To ensure good transport and interaction with water based liquids, the block copolymer may have a contact angle of less than 90°, or <70°, or <50°, or for example <40° when processed into a film according to the method herein.

Soft Block(s), Hard Blocks and Hydrophilic Block(s)

A block is typically composed of the same or similar monomeric units. Wherein same monomeric unit refers to monomeric units having the same chemical structure and similar refers to monomeric units selected from a given group, such as a group consisting of soft monomeric units, a group consisting of hard monomeric units or a group consisting of hydrophilic monomeric units i) Soft Block(s) (A)

A soft block typically comprises monomeric units which in the form of a polymeric block will give a soft block. Thus, such monomeric units are herein referred to as "soft monomeric units" and may be selected from the group consisting of butadiene, isoprene, $C_2$-$C_{30}$-alkyl-substituted 1,3-dienes, $C_1$-$C_{30}$-alkyl acrylates; hydrogenated versions of butadiene, hydrogenated versions of isoprene, hydrogenated versions of $C_2$-$C_{30}$-alkyl-substituted 1,3-dienes and combinations thereof.

In some embodiments, the soft monomeric units may be selected from the group consisting of butadiene, isoprene, $C_2$-$C_{30}$-alkyl-substituted 1,3-dienes, $C_4$-$C_{10}$-alkyl acrylates; hydrogenated versions of butadiene, hydrogenated versions of isoprene, hydrogenated versions of $C_2$-$C_{30}$-alkyl-substituted 1,3-dienes and combinations thereof.

For example, the soft monomeric units may be isoprene or butadiene.

Generally, the soft block may not be hydrophilic. For example, typically, the soft block may not comprise the hydrophilic monomeric units listed below.

The at least one soft block has a number average molecular weight of 20 000-200 000 g/mol, for example 30 000-60 000 g/mol.

Typically, a soft block has a glass transition temperature of less than 20° C., or less than 15° C., or less than 10° C., for example less than 0° C.

ii) Hard Block (B)

The at least two hard blocks typically comprise monomeric units which in the form of a polymeric block will give a hard block. Thus, such monomeric units are herein referred to as "hard monomeric units" and may be selected from the group consisting of styrene, $C_1$-$C_{30}$-alkyl-substituted styrenes, $C_1$-$C_{30}$-alkyl methacrylates, $C_1$-$C_3$-alkyl methacrylamides and combinations thereof.

In some embodiments, the hard nonnumeric units may be selected from the group consisting of styrene, $C_1$-$C_{30}$-alkyl-substituted styrenes, $C_1$-$C_4$-alkyl methacrylates, $C_1$-$C_3$-alkyl methacrylamides and combinations thereof.

Generally, the hard block may not be hydrophilic. For example, typically, the hard block may not comprise the hydrophilic monomeric units listed below.

Each of the at least two hard blocks have a number average molecular weight of 4 000-20 000 g/mol, for example 8 000-15 000 g/mol.

Typically, the hard block has a glass transition temperature of more than 40° C., or more than 50° C., or more than 6β° C.

iii) Hydrophilic Block (C)

The hydrophilic block can be obtained by polymerizing hydrophilic monomers, or by polymerizing monomers which can be rendered hydrophilic by means of chemical reaction in a subsequent step. Irrespective of the chemical procedure, "hydrophilic monomer unit" as used herein refers to the structure of the monomers in the final block copolymer. Thus, both, monomers which are hydrophilic before polymerization and monomers which have been treated hydrophilic by means of a chemical reaction after polymerization will be referred to as hydrophilic monomer units.

Thus, it may be appreciated that the hydrophilic block may be prepared by polymerizing monomers which not hydrophilic, but capable of being rendered hydrophilic by subsequent chemical reactions, into a "hydrophilic block precursor" and subsequently transforming the hydrophilic block precursor into the hydrophilic block (C).

Typical hydrophilic monomer units may be selected form the group consisting of acrylic acid and salts thereof, methacrylic acid and salts thereof, itaconic acid and salts thereof, dialkylaminoacrylates and quaternary salts thereof, dialkylaminomethacrylates and quaternary salts thereof, dialakylaminoacrylamides and quaternary salts thereof, dialakylaminomethacrylamides and quaternary salts thereof, quaternary salts of vinyl pyridine, ethyleneoxide and ethylene oxide-alkylene oxide copolymers, styrene sulfonic acid and salts thereof and ethylene oxide macromers of acrylates or methacrylates; and combinations thereof.

In some embodiments, the hydrophilic monomer units may be selected from the group consisting of acrylic and salts thereof; methacrylic acid and salts thereof, dialkylaminomethacrylates, dialakylaminomethacrylamides, ethyleneoxide and alkylene oxide copolymers, styrene sulfonic acid and salts thereof, and ethylene oxide macromers of acrylates or methacrylates.

The hydrophilic block may comprise 5-50%, or 15-30% by weight of the block copolymer. In embodiments comprising more than one hydrophilic block, the sum of all weights of the hydrophilic blocks comprise 5-50%, or 15-30% relative to the weight of the entire final block copolymer.

The hydrophilic block may have a number average of molecular weight in the range from 1400-240 000 g/mol. In some embodiments, the hydrophilic block may have a number average of molecular weight in the range from 4 200-72 000 g/mol.

The hydrophilic block (C), may comprise at least 10 hydrophilic monomer units directly bound to each other.

Coated Substrates

The block copolymer may be coated onto the respective substrate by applying it in any form, for example in the form of a melt, such as a hot melt, or in form of the coating composition described herein.

The coated substrates may be coated such that the block copolymer is applied to at least a part of their surface area.

In embodiments wherein the substrate is a fibrous substrate, such as a woven web or a nonwoven web, the block copolymer may be applied to the fibers and the woven or nonwoven web may be formed form the coated fibers.

In some embodiments, the coated substrate may comprise from 0.01% to 15%, or from 0.1% to 5% for example from 0.5% to 2% of block copolymer relative to the weight of the (uncoated) substrate.

Coating Composition

The block copolymer herein may be applied to the substrate per se, or in the form of a coating composition.

In some embodiments wherein the substrate is a fibrous substrate, such as a woven or nonwoven web, the block copolymer herein may be applied to the fibers per se, or in the form of a coating composition, before the woven or nonwoven web is formed.

When applied to the substrate as a coating composition, it may comprise a carrier and the block copolymer described below. The carrier may typically be a solvent, such as THF (tetrahydrofuran), toluene, di-n-hexyl phthalate, ethyl acetate, diamyl phthalate, dibutyl sebacate, benzene, chloroform, dibutyl phthalate or methyl ethyl ketone.

Generally, the carrier may be present in any suitable amount such as from 1% to 99%, or from about 30% to about 95%, relative to the weight of the coating composition.

In some embodiments, the carrier may only be present in low amounts, such as 1-10%, or 2-5% relative to the weight of the coating composition.

In some embodiments, the coating composition typically comprises at least 85 wt %, or 90 wt %, for example 95 wt % of the block copolymer described below relative to the weight of the coating composition. In some embodiments, the coating composition consists of the block copolymer.

In some embodiments, higher amounts of carrier may be desirable, such as from 10% to 99%, or from 30% to 95%, relative to the weight of the coating composition.

Optionally, the coating composition may further comprise small amounts of other ingredients, such as antioxidants, UV-stabilizers, organic or inorganic fillers and/or surfactants. Small amount herein typically refers to amounts of less than 2 wt %, or less than 1 wt %, for example less than 0.1 wt % relative to the weight of the coating composition.

Typically, when the block copolymer is applied to the substrate in form of the described coating composition to form the coated substrate, the carrier may not be present in the coating which has been formed. Typically the carrier is evaporated from the coating. However, small amounts may remain present such as less than 5%, or less than 3%, or for example less than 1% by weight of the block copolymer.

Process for Making the Coated Substrate

The process may comprise the steps of:
a) obtaining a substrate;
b) simultaneously with or subsequently to step a), applying the block copolymer or the coating composition comprising the block copolymer to at least a part of said substrate; and optionally the step of
c) annealing the resulting coated substrate of step b),
to obtain the coated substrate herein.

The coating step b) may be done by any known method, for example by immersing the substrate in the coating composition or in a melt comprising the block copolymer; by spraying the coating composition or a melt comprising the block copolymer onto the substrate; by dip-coating the substrate in the coating composition or in a melt comprising the block copolymer. The block copolymer or coating composition comprising the block copolymer, may also be applied by processes known as ring rolling, kiss coating, slot coating, curtain coating, gravure coating/printing, flexographic coating/printing, roll coating, knife coating, meter rod coating, slide coating, gap coating, or spin coating.

In some embodiments, the coating composition may be applied as a solution by dip coating, or kiss coating.

In an alternative embodiment of the invention, the coating step b) may be done by applying the coating composition in the form of a foam, for example an open-cell foam, leading to a porous coating. In yet an alternative embodiment the coating step may be done by forming a fibrous network on the surface of the superabsorbent material such as for example by applying the coating composition in the form of meltblown microfibers, such that an essentially connected coating is formed.

For its application to the substrate, the coating composition may comprise solvents, such as THF (tetrahydrofuran), toluene, di-n-hexyl phthalate, ethyl acetate, diamyl phthalate, dibutyl sebacate, benzene, chloroform, dibutyl phthalate or methyl ethyl ketone.

In embodiments where the coating composition is provided in the form of a solution or a dispersion, processing aids may be added subsequently or prior to the coating step b), e.g. in order to aid a good film formation of the coating.

In the optional step c), the resulting coated substrate may be annealed. The optional annealing step c) typically leads to a further strengthened or more continuous or more completely connected coating and it may eliminate defects.

Typically, the annealing step) involves a heat treatment of the coated substrate; it may be done by for example radiation heating, oven heating, convection heating, azeotropic heating, and it may for example take place in conventional equipment used for drying. In some embodiments, a vacuum may be applied as well. In alternative embodiments, the annealing may be done under an inert gas (to avoid oxidation).

The annealing step typically involves heating the coated substrates at a temperature which is above the highest Tg of the block copolymer, such as to a temperature which is at least 20° C. above said highest Tg, for example at least 50° C. above the highest Tg.

On the other hand, if the substrate has a melting temperature Tm, then the annealing step should be conducted at least 20° C. below the Tm and if possible and at least 20° C., for example at least 50° C. above the highest Tg.

Generally, the substrate as well as the coating shall not be heated to a temperature above their decomposition temperature.

The annealing step may be done for, for example, at least 5 minutes, or for at least 10 minutes or for at least 15 minutes, or at least 30 minutes or at least 1 hour for example at least 2 hours.

This annealing step may be done once, or it may be repeated, for example the annealing step may be repeated with different temperatures, for example first at a lower temperature, and subsequently at a higher temperature.

Typically, the temperature and time are adjusted in order to allow good coating (film) formation, such as to increase the mechanical stability of the coatings.

During the annealing step, the coated substrate may also be dried at the same time. Alternatively or in addition, a separate drying step may be conducted.

In some embodiments, the annealing and/or drying step(s) may be conducted by passing the substrate between heated rolls or nips. Alternatively or in addition the substrate may be treated with UV irradiation.

The process may also involve addition of further processing aids in any of the steps, such as flow aids, drying aids. Any flow aids known in the art may be added (for example prior to or during the coating step, or optionally during the drying and/or annealing step; for example Aerosil 200, available from Degussa has been found to be a good flow aid).

For example, the process may involve addition of a spreading aid and/or surfactant which facilitates the coating step b).

In embodiments wherein the fibers are coated with the block copolymer before they are assembled into a substrate, the process may comprise the following steps a) obtaining fibers;
b) simultaneously with or subsequently to step a), applying the block copolymer or the coating composition comprising the block copolymer to at least a part of said fibers to obtain coated fibers; forming a woven or nonwoven web from the coated fibers to obtain a coated substrate and optionally the step of
c) annealing the coated fibers and/or the coated substrate of step b), to obtain the coated substrate herein.

The coated substrates of the invention are generally useful in a number of applications, for example in absorbent articles, packages or functional (breathable) clothing.

Absorbent Articles

The coated substrates described herein may be used in any part of an absorbent article.

Absorbent articles include diapers, feminine hygiene products and wipes. Examples include but are not limited to disposable absorbent articles, such as disposable diapers, interlabial products, sanitary napkins, panty liners, and adult incontinent products, training pants, dry wipes and wet wipes.

Typically, an absorbent article comprises an absorbent core. It may further comprise a topsheet, which is generally in contact with the wearer when the article is worn.

Optionally, the absorbent article may comprise parts including but not limited to a backsheet which faces towards the garment of the wearer, a core wrap enclosing the absorbent material and/or an acquisition system, typically positioned between the absorbent core and the topsheet.

The coated substrates described herein may generally be used in any part of an absorbent article, for example in parts being in contact with exudates/liquids (e.g., urine, menses, and/or runny feces) and/or intended for promoting rapid transfer of such exudates/liquids.

In some embodiments, they may for example be used in parts of the absorbent article which are in contact with the wearers body when the article is worn, and/or in parts intended for exudates/liquid handling, such as in an absorbent core, for example as a core wrap, as a topsheet, in an acquisition system.

Diaper

In the following, a diaper is described as one embodiment of an absorbent article. However, as the skilled person is aware of, most of the components and materials described herein below are also applicable to other incontinence products such as training pants or adult incontinence products.

The diaper has a longitudinal axis and a transverse axis. The diaper has further an inner, body facing surface and an outer, garment facing surface opposed to the inner surface.

One end portion of the diaper is configured as a front waist region (which is the front one third of the article, having one third of the length of the article). The opposite end portion is configured as a back waist region (back one third) of the diaper, having one third of the length of the article. An intermediate portion of the diaper is configured as a crotch region (centre one third), which extends longitudinally between the front and back waist regions, also having one third of the length of the article. The crotch region is that portion of the diaper which, when the diaper is worn, is generally positioned between the wearer's legs.

The chassis of the diaper comprises the main body of the diaper. The chassis comprises typically a topsheet, which may be liquid pervious, and which may, for the purpose of the invention, comprise or be made of a coated substrate as described herein. Suitable exemplary topsheets are described below.

The chassis typically also comprises a backsheet. The chassis further includes an absorbent core encased between the topsheet and the backsheet. Said backsheet may typically be a liquid impervious backsheet, as known in the art. In one embodiment, the liquid impervious backsheet comprises a thin plastic film such as a thermoplastic film having a thickness of about 0.01 mm to about 0.05 mm. Suitable backsheet materials comprise typically breathable material, which permit vapors to escape from the absorbent article while still preventing exudates from passing through the backsheet. Suitable backsheet films include those manufactured by Tredegar Industries Inc. of Terre Haute, Ind. and sold under the trade names X15306, X10962 and X10964. The backsheet, or any portion thereof, may be elastically extendable in one or more directions. The absorbent core mentioned above may comprise any absorbent material that is generally compressible, conformable, non-irritating to the wearer's skin, and capable of absorbing and retaining liquids such as urine and other body exudates.

The diaper typically has also leg cuffs and/or barrier cuffs. Typically, the diaper may have a pair of opposing (elasticated) leg cuffs, including so-called side panels, and/or a pair of opposing (elasticated) barrier cuffs that provide improved containment of liquids and other body exudates. The cuffs of a pair may be mirror images of one another in the y-axis (longitudinal axis) of the article. Suitable cuffs are described in for example U.S. Pat. No. 3,860,003; U.S. Pat. Nos. 4,808, 178 and 4,909; U.S. Pat. Nos. 4,695,278 and 4,795,454.

Further, the diaper may comprise a front and back waist band and/or a fastening system, typically joined to the waistband, as known in the art. Preferred fastening systems comprise fastening tabs and landing zones, wherein the fastening tabs are attached or joined to the back region of the diaper and the landing zones are part of the front region of the diaper.

Processes for assembling the diaper include conventional techniques known in the art for constructing and configuring disposable absorbent articles. For example, the backsheet and/or the topsheet can be joined to the absorbent core or to each other by a uniform continuous layer of adhesive, a patterned layer of adhesive, or an array of separate lines, spirals, or spots of adhesive. Adhesives which have been found to be satisfactory are manufactured by H. B. Fuller Company of St. Paul, Minn. under the designation HL-1258 or H-2031.

Feminine Hygiene Product

In the following, a feminine hygiene product is described (e.g., sanitary napkin or panty-liner). A feminine hygiene product may comprise a topsheet which as described further below, a backsheet, and an absorbent core positioned between the topsheet and backsheet; each component having a body facing surface and a garment facing surface. The topsheet may be made of a coated substrate as described herein. The backsheet can be any known or otherwise effective backsheet material, provided that the backsheet prevents external leakage of exudates absorbed and contained in the feminine hygiene article. Flexible materials suitable for use as the backsheet include, but are not limited to, woven and nonwoven materials, laminated tissue, polymeric films such as thermoplastic films of polyethylene and/or polypropylene, composite materials such as a film-coated nonwoven material, or combinations thereof, as is well known in the art of making feminine hygiene articles such as sanitary napkins, pantiliners, and the like.

The feminine hygiene product also comprises an absorbent core. The absorbent core is typically positioned between the topsheet and the backsheet. The size and shape of the absorbent core can be altered to meet absorbent capacity requirements, and to provide comfort to the wearer/user. The absorbent core suitable for use in the present invention can be any liquid-absorbent material known in the art for use in absorbent articles, provided that the liquid-absorbent material can be configured or constructed to meet absorbent capacity requirements.

The feminine hygiene product may also comprise wings which may enable attachment to the underwear of the wearer. The sanitary napkins and/or panty-liners herein may comprise a fastening means comprised by the backsheet and/or by the wings. For example, adhesive attachment means are present on or attached to at least the backsheet.

Topsheets Comprising or Being Made of the Coated Substrate

The topsheet may comprise or be made of a hydrophilic substrate that promotes rapid transfer of liquids (e.g., urine, menses, and/or runny feces) through the topsheet.

Thus, in some embodiments at least a portion of the topsheet may be coated with the block copolymer described herein. In some embodiments, at least a portion of the wearer facing surface area of the topsheet may be coated with the block copolymer, for example at least 60% of the wearer facing surface of the topsheet may be coated with the block copolymer.

The topsheet itself is typically made of a hydrophobic material, at least a portion of the wearer facing surface of the topsheet may coated with the block copolymer so that liquids will transfer through the topsheet more rapidly. This diminishes the likelihood that body exudates will flow off the topsheet rather than being drawn through the topsheet and being absorbed by the absorbent core.

The topsheet is generally pliant, soft feeling, and non-irritating to the wearer's skin. Further, the topsheet is liquid pervious, permitting liquids (e.g., menses, urine, and/or runny feces) to readily penetrate through its thickness.

A suitable topsheet may be manufactured from a wide range of materials such as woven and nonwoven materials (e.g., a nonwoven web of fibers); polymeric materials such as apertured formed thermoplastic films, apertured plastic films, and hydroformed thermoplastic films; porous foams; reticulated foams; reticulated thermoplastic films; and thermoplastic scrims.

Suitable woven and nonwoven materials can be comprised of natural fibers (e.g., wood or cotton fibers), synthetic fibers (e.g., polymeric fibers such as polyester, polypropylene, or polyethylene fibers) or from a combination of natural and synthetic fibers. When the topsheet comprises a nonwoven web, the web may be manufactured by a wide number of known techniques. For example, the web may be spunbonded, carded, wet-laid, melt-blown, hydroentangled, combinations of the above, or the like.

Additionally, the topsheet may be elasticized to provide storage compartments or separation means for body exudates, particularly bowel movements. Such topsheets and articles containing them are detailed in U.S. Pat. No. 6,482,191.

In some embodiments, the topsheet may be elasticized (i.e. a topsheet may comprise an elastomeric martial alone or in combination with elastic strands, such as rubber strands.

A coated substrate as described herein may be comprised by, or may form, or may be used for manufacturing of, the topsheet of an absorbent article.

The substrate comprised by, or forming, or used for manufacturing of, the topsheet of an absorbent article may alternatively, or additionally be apertured, i.e. the topsheet has a plurality of apertures having an aperture size of at least about $0.2 \text{ mm}^2$. The topsheet may have an open area of at least about 10%, the open area being the sum of all apertures. The open area are may be determined by the procedure disclosed in WO 95/05139.

The substrate may be comprised by, or may form, or may be used for manufacturing of a topsheet that has one or more openings. Typically, the openings are large enough to let feces or menses pass to a void space underneath said topsheet, also referred to as anal cuff or vaginal cuff. For example, U.S. Patent Application No. 2006/0058766 A, filed on Sep. 13, 2005 discloses an absorbent article wherein the topsheet is provided with at least one opening adapted to receive fecal material. Such topsheets may be made of or may comprise a liquid impervious material, and thus, the substrate may be a liquid impervious material.

Absorbent Core Comprising the Coated Substrate

The absorbent core has two major sides, a first side facing the body of the wearer when the absorbent article is worn and a second side facing the garment when the absorbent article is worn. Accordingly, the first and second side may also be referred to as body-facing and garment facing side.

The absorbent core has a length along an x-axis, a width, smaller than the length, along a y-axis and a height, smaller than the width, along a z-axis.

In certain embodiments, the absorbent core may be of rectangular shape. In other embodiments the core may have curved edges. For example, the core may be of an hourglass shape.

The absorbent core may comprise a core wrap and absorbent materials which are known to those skilled in the art. Optionally, the absorbent core comprises one or more glues, surfactants, binders, colors, pigments, perfume, lotion(s), opacity enhancers, nonwovens, odor control materials or materials to increase the dry/wet integrity of the core, such as structural elements.

The core wrap may comprise or be made of a coated substrate described herein.

The core wrap is used to cover the absorbent material. In certain embodiments the absorbent material and, if present, the glue, such as a microfibrous glue, may either be sandwiched between two separately provided sheets of core wrap material, or may be wrapped by folding one sheet of core wrap material, for example in a C-fold, to envelope the absorbent material and, optionally, the glue, for example the microfibrous glue.

In one embodiment the absorbent core may for example comprise as a core wrap a nonwoven web, such as nonwoven web coated with the block copolymer as described herein. The absorbent material, such as the superabsorbent polymer material may then be deposited on the nonwoven fabric. If present, the glue may be deposited such that it at least partly covers or enlaces the absorbent material on the nonwoven fabric.

The amounts of materials used in the absorbent core herein are given in % by weight relative to the basis weight of the whole absorbent core including the core wrap. The basis weight of the absorbent core is given in $g/cm^2$. The basis weight may be determined by weighing the whole absorbent core. The obtained weight is then divided by the area enclosed by the perimeter line.

The absorbent core may comprise a relatively high amount of superabsorbent polymer material of more than 80%, 85%, 90%, or 95% by weight of the absorbent core.

In certain embodiments, the absorbent core comprises less than 20%, or 15% or 10% or 5% by weight of the absorbent core of airfelt material.

In one embodiment, the absorbent core may be substantially free of, or completely free of airfelt material wherein "substantially free of" means that less than 1% by weight of the absorbent core comprises airfelt material and "completely free of" means that 0% by weight of the absorbent core consist of airfelt material.

According to certain embodiments, the absorbent core consists essentially of superabsorbent polymer material, glue and a core wrap. In such an embodiment the amounts of these materials may add up to present up to 99%, for example 100% by weight of the absorbent core.

Wipes Comprising the Coated Substrate

In the following a wipe is described. The wipe may be made of a coated nonwoven substrate as described herein above.

Whilst not limited to a particular use, where the substrate is used for manufacturing of wipes (e.g., wet wipes), it may be intended for cleaning the body, in particular the peri-anal area after defecation and/or the external genital area after urination of babies, toddlers and adults. Other examples of use of the substrate when in the form of wipes include feminine hygiene wipes.

The present invention also encompasses the combination of absorbent articles described herein (e.g., diaper including a topsheet comprising a coated substrate as described herein) with wipes comprising a coated substrate as described herein.

EXAMPLES

Monomer Purification

Monomers are purified to a grade suitable for conducting living anionic polymerization reactions. Means of purification, as for example described with regard to isoprene or styrene in the context of example 1, are known to those skilled in the art.

Example 1 synthesis of block-copolymer
poly(styrene-b-isoprene-b-styrene) precursor

Styrene Purification

Styrene (Aldrich) is purified by passing through an activated alumina (available from Aldrich) column under nitrogen atmosphere to remove inhibitors and then the styrene is added to a clean, dry round bottom flask filled with nitrogen and fitted with rubber septa.

Isoprene Purification

Isoprene (Aldrich) is purified by passing through an activated alumina column under nitrogen atmosphere to remove inhibitors and then the isoprene is added to a clean, dry round bottom flask filled with nitrogen and fitted with rubber septa.

To a clean reactor at 60° C., is added 3 liters of cyclohexane (pesticide residue analysis (PRA) grade from Aldrich) and 60 g of styrene (Aldrich). This is titrated with s-butyl lithium to a persistent yellow color and 5 mmole of butyl lithium is added to give the desired molecular weight. After 20 minutes a sample is taken and 280 grams of isoprene (Aldrich) is added to the reactor. This is allowed to react for 45 minutes maintaining the temperature at 60° C. A sample is taken for analysis and 60 grams of styrene is added. After 20 minutes a 20 gram sample is taken for analysis and testing. The living polymer anion is then ready for further reaction in subsequent examples.

The molecular weight of the first block is found to be 12,800 g/mole. The triblock is found to have a molecular weight of 80,000 g/mole with a composition of 27 weight percent styrene, 73 weight percent isoprene.

Example 2

Synthesis of poly(styrene-b-isoprene-b-styrene-t-tert-butylmethacrylate)

500 ml of the reaction product from Example 1 is diluted in 1500 ml of THF containing 2.5 mmole of 1,1-diphenylethylene (Aldrich) and then cooled to −78° C. To this solution is added 37.5 grams of purified t-butyl methacrylate (TCI America). After 20 minutes, 1 ml of methanol is added. The reaction is warmed to room temperature and the polymer is isolated by precipitation from methanol. The polymer is stabilized by addition of 0.2 g of Irganox 1010 (Ciba). The polymer is found to have a molecular weight of 100K g/mole with a composition of 30 weight percent (poly)t-butylmethacrylate.

Example 3

Synthesis of poly(styrene-b-isoprene-b-styrene-b-glycidylmethacrylate)

500 ml of the reaction product from Example 1 is diluted in 1500 ml THF containing 2.5 mmole of 1,1-diphenylethylene (Aldrich) and then cooled to −78° C. To this solution is added 5 grams of purified glycidyl methacrylate (Aldrich).

Example 4

Synthesis of poly(styrene-b-isoprene-b-methacrylic acid 25 grams of the poly(styrene-b-isoprene-b-styrene-b-tert-butylmethacrylate) material from Example 2 is dissolved in 500 ml of toluene (Aldrich) and to this added 0.2 grams of p-toluene-sulfonic acid (Aldrich) along with 0.5 grams of Irganox 1010 (Ciba). The reaction is heated to reflux and isobutylene gas is evolved over a period of minutes. After 45 minutes of reflux, the solution is cooled and the product is isolated by precipitation from methanol (Aldrich). 0.1 g of Irganox 1010 (Ciba) is added to the polymer which is then vacuum dried.

Example 5

Synthesis of poly(styrene-b-isoprene-b-styrene-b-methacryoxy-polyethylene oxide (1K))

500 ml of the poly(styrene-b-isoprene-b-styrene-b-glycidylmethacrylate) material from Example 3 is reacted with 50 grams of Jeffamine M1000 polymer from Huntsman Chemical. The product obtained is poly(styrene-b-isoprene-b-styrene-b-methacryoxy-polyethylene oxide).

Example 6

Synthesis of poly(styrene-b-isoprene-b-styrene-b-methacryoxy-polyethylene oxide (2K))

500 ml of the poly(styrene-b-isoprene-b-styrene-b-glycidylmethacrylate) material from Example 3 is reacted with 50 grams of Jeffamine M-2070 polymer from Huntsman Chemical. The product obtained is poly(styrene-b-isoprene-b-styrene-b-methacryoxy-polyethylene oxide).

Example 7

Synthesis of poly(styrene-b-t-butylstyrene-b-1,2-butadiene-b-tbutylstyrene)

To a clean reactor at 25 C, is added 3 liters of cyclohexane (PRA grade from Aldrich) and 3.6 grams of Tetrahydrofuran (Aldrich) and 62 grams of styrene (Aldrich). This is titrated with s-butyl lithium to a persistent yellow color and 3.1 mmole of s-butyl lithium is added to give the desired molecular weight. After 20 minutes a sample is taken and 27 grams of t-butyl styrene (Aldrich) and this is allowed to react for 30 minutes. After 30 minutes a sample is taken and 112 grams of butadiene (Electronics grade Matheson Gas) is added to the reactor. This is allowed to react for 240 minutes maintaining the temperature at 25° C. A sample is taken for analysis and 27 grams of t-butyl styrene is added. After 20 minutes the reaction is terminated by addition of methanol. The reaction solution is stabilized with 0.25 grams of Irganox 1010 and vacuum dried.

Example 8

Preparation of Nickel Hydrogenation Catalyst

Hydrogenation catalyst is prepared as follows; 0.345 g of nickel (2-ethyl hexanoate) (Aldrich) is dissolved in 30 ml of cylcohexane (PRA grade VWR). To this is added 3 ml of triethylaluminum (Aldrich) (1.0M in hexanes) resulting in a black dispersion of nickel catalyst.

Example 9

Synthesis of poly(styrene-t-butylstyrene-b-ethylene-butene-b-t-butylstyrene)

100 grams of the poly(styrene-b-t-butylstyrene-b-1,2-butadiene-b-t-butylstyrene) from Example 7 is dissolved in 2000 ml of cyclohexane and the butadiene block is hydrogenated with a Nickel catalyst as prepared in example 8. The catalyst is added via syringe to the polymer solution and hydrogen gas is added to the reaction at 50 psi with stirring until substantially complete hydrogenation of the butadiene block occurs. Samples are taken for analysis to confirm hydrogenation of the butadiene block and an additional batch of catalyst is required to complete the hydrogenation.

Example 10

Preparation of Acetyl Sulfate

A solution of acetyl sulfate is prepared as follows. To 100 ml of methylene chloride (Aldrich) is added 200 ml of acetic anhydride (Aldrich) and this is cooled to 0° C. To this is slowly added 55.5 ml of sulfuric acid (Aldrich). This is allowed to react for 60 minutes at 0° C.

Example 11

Synthesis of poly(styrenesulfonate-b-t-butylstyrene-b-ethylene-butene-b-t-butylstyrene)

20 grams of the poly(styrene-b-t-butylstyrene-b-ethylene-butene-b-t-butylstyrene) from example 9 is dissolved in methylene chloride (Aldrich) at 0° C., to which is added 100 ml of the acetyl sulfate prepared in Example 10. This is reacted for 120 minutes to prepare the poly(styrenesulfonate-b-t-butylstyrene-b-ethylene-butene-b-t-butylstyrene).

Example 12

Synthesis of poly(styrene-b-isoprene-b-styrene-b-methacrylic acid diethanolamine salt 10 grams of the polymer from Example 4 is dissolved in 100 ml of THF (Aldrich) and neutralized with 1.3 grams of diethanolamine. The solution is cast into a Teflon dish to form a film with a diameter of 4 inches.

Example 13

10 grams of the polymer from Example 5 is dissolved in 100 ml of THF (Aldrich). 12 mL of the solution is cast into a flat bottomed 4 inch Teflon dish to form a film. The solvent (typically THF) is allowed to evaporate at 25° C. and 40-60% humidity overnight and subsequently vacuum dried at 40° C. for 16 hours. After that, the film is peeled from the dish. Suitable sample sizes are cut from the film. DSC analysis of the polymer indicates glass transition temperatures at −61 C and at +65 C.

Example 14

10 grams of the polymer from Example 6 is dissolved in 100 ml of THF (Aldrich). 12 mL of the solution is cast into a flat bottomed 4 inch Teflon dish to form a film. The solvent (typically THF) is allowed to evaporate at 25° C. and 40-60% humidity overnight and subsequently vacuum dried at 40° C. for 16 hours. After that, the film is peeled from the dish. Suitable sample sizes are cut from the film. DSC analysis of the polymer indicates glass transition temperatures at −61 C and at +64 C.

Example 15

10 grams of the polymer from Example 11 is dissolved in 100 ml of THF (Aldrich). 12 mL of the solution is cast into a flat bottomed 4 inch Teflon dish to form a film. The solvent (typically THF) is allowed to evaporate at 25° C. and 40-60% humidity overnight and subsequently vacuum dried at 40° C. for 16 hours. After that, the film is peeled from the dish. Suitable sample sizes are cut from the film. DSC analysis of the polymer indicates glass transition temperatures at −53 C and at +57 C.

Example 16

10 grams of the polymer from Example 1 is dissolved in 100 ml of THF (Aldrich). 12 mL of the solution is cast into a flat bottomed 4 inch Teflon dish to form a film. The solvent (typically THF) is allowed to evaporate at 25° C. and 40-60% humidity overnight and subsequently vacuum dried at 40° C. for 16 hours. After that, the film is peeled from the dish. Suitable sample sizes are cut from the film. DSC analysis of the polymer indicates glass transition temperatures at −61 C and at +65 C.

Examples 17-21

Films as prepared in examples 12-16 are cut to circles with a diameter of 2⅞ inches which are then mounted into MVTR cups from Gardco (Paul N Gardner Co.) containing deionized water. These cups/water/films are placed on 4 digit balances contained within a dry box and the weight with time measurements are taken for 8 hours. Humidity is kept low by sweeping the box with dry nitrogen gas. The WVTR values are determined from the average rate of three films measured as described.

TABLE 1

WVTR values and contact angles of films prepared form the block copolymer examples

| Sample | Film | Thickness in mm | WVTR in grams/m$^2$/day | Contact Angle |
|---|---|---|---|---|
| Example 17 | Example 12 | 0.15 | 6000 | 38° |
| Example 18 | Example 13 | 0.15 | 1100 | 64° |
| Example 19 | Example 14 | 0.15 | 900 | 78° |
| Example 20 | Example 15 | 0.15 | 2500 | |
| Example 21 | Example 16 | 0.15 | 200 | 104° |

TABLE 2

Wet elongation at break values of films prepared form the block copolymer examples

| Sample | Peak Load in N | Peak Strain in % |
|---|---|---|
| Example 18 | 5.99 | 1141.66 |
| Example 19 | 8.81 | 1991.11 |
| Example 17 | 14.81 | 302.22 |

TABLE 3 structural formulas of block copolymers

| Sample | Blockcopolymer | Chemical formula of block copolymer |
|---|---|---|
| Example 17 | Example 4 | [structure: styrene-isoprene-styrene block with methacrylic acid/methacrylate copolymer block terminating in C=O OH and C=O O⁻ +NHR₃ groups, with subscripts n, m, n, p, p-x] |
| Example 18 | Example 5 | [structure: styrene-isoprene-styrene block with methacrylate block bearing -C(=O)-O-CH₂-CH(OH)-CH₂-NH-PEO side chain, subscripts n, m, n, p] |
| Example 19 | Example 6 | [structure: styrene-isoprene-styrene block with methacrylate block bearing -C(=O)-O-CH₂-CH(OH)-CH₂-NH-PEO side chain, subscripts n, m, n, p] |

TABLE 3-continued structural formulas of block copolymers

| Sample | Blockcopolymer | Chemical formula of block copolymer |
|---|---|---|
| Example 20 | Example 11 | *(structural formula shown)* |
| Example 21 | Example 1 | *(structural formula shown)* |

Methods of Measurement

Film Formation

The polymer films used for the methods herein are prepared by solution casting the film into a flat bottomed 4 inch Teflon® dish using 12 mL of a solution comprising 10 g of the block copolymer dissolved in 100 mL of a solvent. The solvent (typically THF) is allowed to evaporate at 25° C. and 40-60% humidity overnight and subsequently vacuum dried at 40° C. for 16 hours. After that, the film is peeled from the dish. Suitable sample sizes are cut from the film.

Water Vapor Transmission Rate (WVTR)

Using the ASTM method E 96-80 as a guide, the water vapor transmission of polymers is tested via the water method using Gardco cups. These cups have an opening of 5.64 cm in diameter, which corresponds to an open surface area of 25 square cm.

The films are cut to a diameter of $2_{7/8}$ inches with a film punch.

Two 3 mm holes are punched into the film on opposite sides for mounting the film over the pins of the cup to secure the film in position.

The cup is partially filled with water leaving an air space of at least ¼ inch above the water level. The cup is coated with a silicone grease around the edge and the film is pushed down into the silicone and the top of the cup is tightened down onto the edges of the polymer film.

Sample cups are placed onto a balance having an accuracy of +/−0.0001 g in an environmental enclosure with continuous nitrogen purge to maintain low humidity. The enclosure humidity is monitored with time to confirm the relative humidity is below 10%.

The weights of the samples are taken at one minute intervals for 16 hours with the WVTR value determined over the first 4 hours of the experiment.

The data is plotted weight change versus time in hours, and the slope is taken with units of grams/25 sq cm/hour. Translation of this to grams/sq meter/day involves multiplying the slope of the data by 9600. The value 9600 comes from the factor of 24 hours per day and a factor of 40 to convert the 25 sq cm opening to square meters.

Contact Angle Measurement

The contact angle measurements where conducted using the ASTM method D5946-09 as a guide. All testing has been conducted at a temperature of 25° C. and a relative humidity of 60-70°. The following adaptations have been made:

7. Apparatus: 7.1 *Contact Angle Meter, or Goniometer*—The experiments have been conducted on a FTA 200 from First Ten Angstroms, Inc.
8. Reagents and Materials: 8.1 *Purity of Water*—Millipore water has been used for the testing purposes.
9. Sampling: 9.1 Films of the size of 1 cm×1 cm have been used for the contact angle measurement.
10. Conditioning: 10.1 No special conditioning has been performed on the films.
11. Procedure: 11.2 Suspend a 5 to 8-μL droplet at the end of a blunt ended 22 gauge syringe needle from a 10 ml syringe. 11.3 Within 5 sec of the drop transferring to the film an image is taken. The image is then analyzed by the First Ten Angstrom software package. 11.4 Advance the sample to place the next droplet onto a previously untouched area. 11.5 Take three contact angle measurements on the sample.
12. Calculation: 12.1.1 Calculate the average of the three measurements.

Wet-Elongation at Break Test

This test method is used to measure the wet-elongation at break (=extensibility at break). A preferred piece of equipment to do the tests is a tensile tester such as an Instron 5544, fitted with a computer interface and heated environmental chamber and Bluehill Software, available from Instron Corporation with a 100N load cell. This measures the Constant Rate of Extension in which the pulling grip moves at a uniform rate. The load cell is selected such that the measured load (e.g., force) of the tested samples be between 10 and 90% of the capacity of the load cell.

Each sample is die-cut from a film, each being 2"×0.5" using a die cutter with a clicker press to cut the film into individual samples A minimum of three samples are chosen which are substantially free of visible defects such as air bubbles, holes, inclusions, and cuts. They should also have smooth and substantially defect-free edges.

The samples are then swollen in 0.9% Saline overnight at 25° C. before being tested.

The samples are then removed from the saline and the excess saline is allowed to drain off the sample before it is loaded into pneumatic line grips with a gage length of one inch that are attached to the precalibrated 100 N Load Cell on the Instron 5544 Testing System running the Bluehill software package with its environmental chamber set to 38° C. The sample is then strained at a rate of 254 mm/min (10 in/min) until it breaks. The force (N) and strain (%) at which it breaks is then recorded.

Glass Transition Temperatures

Glass Transition Temperatures (Tg's) are determined for the purpose of this invention by differential scanning calorimetry (DSC). The calorimeter should be capable of heating/cooling rates of at least 20° C./min over a temperature range, which includes the expected Tg's of the sample that is to be tested, e.g. of from −90° to 250° C., and the calorimeter should have a sensitivity of about 0.2 µW. TA Instruments Q1000 DSC is well-suited to determining the Tg's referred to herein. The material of interest can be analyzed using a temperature program such as: equilibrate at −90° C., ramp at 20° C./min to 120° C., hold isothermal for 5 minutes, ramp 20° C./min to −90° C., hold isothermal for 5 minutes, ramp 20° C./min to 250° C. The data (heat flow versus temperature) from the second heat cycle is used to calculate the Tg via a standard half extrapolated heat capacity temperature algorithm. Typically, 3-5 mg of a sample material is weighed (+/−0.1 g) into an aluminum DSC pan with crimped lid.

Herein, $Tg_1$ and $Tg_2$ can be measured on a sample of the sequence of hard and soft block(s) before the hydrophilic block is added.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A substrate coated with a block copolymer, wherein the substrate is selected from the group consisting of woven webs, nonwoven webs, films, and laminates thereof, and wherein the block copolymer is obtainable by the process of:
   (i) preparing a sequence of soft block(s) (A) and hard blocks (B), the sequence comprising at least three blocks being at least a first soft block, a first hard block and a second hard block wherein the first soft block is sandwiched between the first and second hard blocks (B), wherein the first soft block has a number average molecular weight of about 20,000 to about 200,000 g/mol, and wherein each of the at least two hard blocks has a number average molecular weight of about 4,000 to about 20,000 g/mol; and
   (ii) combining the sequence of soft block(s) and hard blocks with a hydrophilic block (C), or combining the sequence of soft block(s) and hard blocks with a hydrophilic block precursor and subsequently transforming the hydrophilic block precursor into the hydrophilic block (C).

2. The substrate of claim 1, wherein the hydrophilic block (C), comprises at least about 10 hydrophilic monomer units directly bound to each other.

3. The substrate of claim 1, wherein the hydrophilic block (C), comprises about 5 to about 50%, by weight, of the block copolymer.

4. The substrate of claim 1, wherein the substrate comprises fibers coated with the block copolymer.

5. The substrate of claim 1, wherein the sequence of soft block(s) and hard blocks has at least two glass transition temperatures $Tg_1$ and $Tg_2$, wherein $Tg_1$ and $Tg_2$ differ by at least about 20° C.

6. The substrate according to claim 5, wherein $Tg_1 \leq$ about 20° C., $Tg_2 \geq$ about 40° C., or both.

7. The substrate of claim 1, wherein the hydrophilic block is comprised of hydrophilic monomeric units comprising one or more functional groups selected from the group consisting of: acid groups in their free acid or salt form, ether groups, amine functionalized groups, quaternary ammonium groups, alcoholic groups, and combinations thereof.

8. The substrate of claim 1, wherein the at least one hydrophilic block comprises monomeric units selected from the group consisting of: acrylic acid and salts thereof, methacrylic acid and salts thereof, itaconic acid and salts thereof, dialkylaminoacrylates and quaternary salts thereof, dialkylaminomethacrylates and quaternary salts thereof, dialakylaminoacrylamides and quaternary salts thereof, dialakylaminomethacrylamides and quaternary salts thereof, quaternary salts of vinyl pyridine, ethyleneoxide and ethylene oxide-alkylene oxide copolymers, styrene sulfonic acid and salts thereof and ethylene oxide macromers of acrylates or methacrylates; and combinations thereof.

9. The substrate of claim 1, wherein the at least one soft block comprises monomeric units selected from the group consisting of butadiene, isoprene, $C_2$-$C_{30}$-alkyl-substituted 1,3-dienes, $C_1$-$C_{30}$-alkyl acrylates; hydrogenated versions of butadiene, hydrogenated versions of isoprene, hydrogenated versions of $C_2$-$C_{30}$-alkyl-substituted 1,3-dienes and combinations thereof; and
   wherein the at least two hard blocks comprise monomer units selected from the group consisting of styrene, $C_1$-$C_{30}$-alkyl-substituted styrenes, $C_1$-$C_{30}$-alkyl methacrylates, $C_1$-$C_3$-alkyl methacrylamides and combinations thereof.

10. The substrate of claim 1, wherein the block copolymer is a tetra-block copolymer wherein the four blocks are arranged in the sequence B-A-B-C.

11. The substrate of claim 1, wherein the block copolymer used for the coating exhibits a WVTR of at least about 600 g/m²/day when processed into a film and measured according to the WVTR method described herein.

12. The substrate of claim 1, wherein the block copolymer used for the coating exhibits a wet-elongation at break value of at least about 300% when processed into a film and measured according to the method herein.

13. The substrate of claim 1, wherein the contact angle measured on a film prepared from the sequence of soft block(s) and hard blocks is higher than the contact angle of the block copolymer when prepared into a film according to the method given herein.

14. The substrate of claim 1, wherein the block copolymer used for the coating has a contact angle of less than about 90° when processed into a film according to the method herein.

15. An absorbent article comprising the coated substrate of claim 1.

16. The absorbent article of claim 15, further comprising an absorbent core, a topsheet, a core wrap and/or an acquisition system, wherein the coated substrate is comprised by one or more of the absorbent core, the topsheet, the core wrap and/or the acquisition system.

17. A process for making a coated substrate comprising the steps of:
  (i) providing the substrate, wherein the substrate is selected from the group consisting of woven webs, nonwoven webs, films, and laminates thereof;
  (ii) providing a block copolymer or a coating composition comprising the block copolymer; and
  (iii) coating the substrate with the block copolymer or the coating composition to form a coated substrate;
  wherein the block copolymer is obtainable by the process of:
  (i) preparing a sequence of soft block(s) (A) and hard blocks (B), the sequence comprising at least three blocks being at least a first soft block, a first hard block and a second hard block wherein the first soft block is sandwiched between the first and second hard blocks (B), wherein the first soft block has a number average molecular weight of about 20,000 to about 200,000 g/mol, and wherein each of the at least two hard blocks has a number average molecular weight of about 4,000 to about 20,000 g/mol;
  (ii) combining the sequence of soft block(s) and hard blocks with a hydrophilic block (C), or combining the sequence of soft block(s) and hard blocks with a hydrophilic block precursor and subsequently transforming the hydrophilic block precursor into the hydrophilic block (C).

18. The process of claim 17, further comprising the step(s) of drying and/or annealing the coated substrate.

* * * * *